United States Patent [19]

Sjoerdsma

[11] 4,437,873

[45] Mar. 20, 1984

[54] METHOD OF INHIBITING ALGAE

[75] Inventor: Albert Sjoerdsma, Cincinnati, Ohio

[73] Assignee: Merrell Dow Pharmaceuticals Inc., Cincinnati, Ohio

[21] Appl. No.: 368,546

[22] Filed: Apr. 15, 1982

Related U.S. Application Data

[63] Continuation-in-part of Ser. No. 246,569, Mar. 23, 1981, Pat. No. 4,336,054, which is a continuation-in-part of Ser. No. 95,347, Nov. 19, 1979, abandoned.

[51] Int. Cl.³ .................................................. A01N 33/04
[52] U.S. Cl. .................................................... 71/67
[58] Field of Search ........................................ 71/67, 121

[56] References Cited

U.S. PATENT DOCUMENTS

| | | | |
|---|---|---|---|
| 2,890,246 | 6/1959 | McKinney et al. | 71/67 X |
| 3,466,162 | 9/1969 | Gloor et al. | 71/67 |
| 3,657,346 | 4/1972 | Duerr et al. | 71/67 X |
| 3,892,806 | 7/1975 | Eckert et al. | 71/67 X |
| 4,134,918 | 1/1979 | Bey et al. | 424/330 X |
| 4,139,563 | 2/1979 | Metcalf et al. | 424/330 X |
| 4,304,590 | 12/1981 | Reinhardt et al. | 71/67 |

FOREIGN PATENT DOCUMENTS

| | | |
|---|---|---|
| 868586 | 10/1978 | Belgium . |
| 868591 | 10/1978 | Belgium . |
| 868882 | 11/1978 | Belgium . |

OTHER PUBLICATIONS

Brachet et al., C. R. Acad. Sci. Paris, Serie D 287, 1289–1292 (1978).

*Primary Examiner*—Catherine L. Mills
*Attorney, Agent, or Firm*—Stephen L. Nesbitt; William J. Stein; Raymond A. McDonald

[57] ABSTRACT

α-Substituted amines are described which are useful in controlling the growth of algae.

5 Claims, No Drawings

METHOD OF INHIBITING ALGAE

DESCRIPTION

This application is a continuation-in-part of U.S. Ser. No. 246,569 filed Mar. 23, 1981, now U.S. Pat. No. 4,336,054 which is a continuation-in-part of U.S. Ser. No. 95,347 filed Nov. 19, 1979, abandoned.

TECHNICAL FIELD

This invention relates to certain α-substituted amines which are useful in controlling or inhibiting the growth of algae.

BACKGROUND ART

Polyamines have been implicated in many aspects of cell division. Impairment of the biosynthesis of polyamines by means of enzyme inhibitors is believed to cause a decrease in cell proliferation in mammals. Although the physiological role of polyamines has not been clearly delineated, there is evidence to suggest their involvement with cell division and growth, H. G. Williams—Ashman et al., The Italian J. Biochem. 25, 5-32 (1976), A. Raina and J. Janne, Med. Biol. 53, 121-147 (1975) and D. H. Russell, Life Sciences 13, 1635-1647 (1973).

Polyamines are also known to be essential growth factors for certain microorganisms, as for example *E. coli*, Enterobacter, Klebsiella, *Staphylococcus aureus*, *C. cadaveris*, *Salmonella typhosa* and *Haemophilus parainfluenza*. There is evidence to suggest that polyamines are associated with both normal and neoplastic mammalian cell growth, there being an increase in both the synthesis and accumulation of polyamines following a stimulus causing cellular proliferation. It is also known that there is a correlation between polyamine formation and the activity of the decarboxylase enzymes of ornithine, S-adenosylmethionine, arginine and lysine. The term polyamine is taken to include the diamine putrescine and the polyamines spermidine and spermine. Putrescine is the decarboxylation product of ornithine, catalyzed by ornithine decarboxylase. Putrescine formation may also occur by decarboxylation of arginine to form agmatine which is hydrolyzed to give putrescine and urea. Arginine is also involved in ornithine formation by action of the enzyme arginase. Activation of methionine by S-adenosylmethionine synthetase forms S-adenosylmethionine which is decarboxylated, after which the propylamine moiety of activated methionine may be transferred to putrescine to form spermidine or the propylamine moiety may be transferred to spermidine to form spermine. Hence, putrescine serves as a precursor to spermidine and spermine and additionally has been shown to have a marked regulatory effect upon the polyamine biosynthetic pathway in that it has been shown that increased synthesis of putrescine is the first indication that a tissue will undergo renewed growth processes. Cadaverine which is the decarboxylation product of lysine has been shown to stimulate the activity of S-adenosylmethionine decarboxylase and is known to be essential to growth processes of many microorganisms, for example, H. parainfluenza.

Very little is known of the role of polyamines in algal growth. The occurrence of polyamines in algae has been reported, but little is known about their biosynthetic pathways in algae. Brachet et al., C.R. Acad. Sc. Paris, Serie D, 287, 1289-92 (1978), has shown that DL-α-methylornithine arrests development of sea Urchine eggs, and prevents the regeneration of the algae, *Acetabularia mediterranea*, via the inhibition of nuclear RNA synthesis.

SUMMARY OF THE INVENTION

I have discovered that compounds belonging to a class of irreversible inhibitors of ornithine decarboxylase are useful in inhibiting the growth of algae. Moreover, this inhibition occurs among the blue-green, green, the diatom and the pigmented flagellate groups of algae. More particularly, the compounds useful in the practice of this invention are α-substituted amines having the general formula

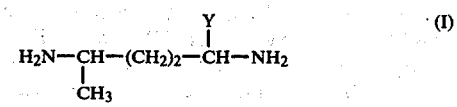

wherein Y is selected from the group consisting of $CH_2F$, $CHF_2$ and $C\equiv CH$; and the salts and individual optical isomers thereof.

Actively growing algae when placed in contact with these compounds demonstrate a reduction in their rate of proliferation and growth, enabling these compounds to be useful for the control of algae in industrial and recreational water supplies.

DETAILED DESCRIPTION OF THE INVENTION

In general formula (I) above the symbol Y is represented by either an acetylenic group or a fluoro-substituted methyl group. The fluoro-substituted methyl group is illustrated by the monofluoromethyl or difluoromethyl radicals.

Illustrative examples of the salts of the compounds of this invention include non-toxic acid addition salts formed with inorganic acids, such as, hydrochloric, hydrobromic, sulfuric and phosphoric acid, and organic acids, such as, methane sulfonic, salicyclic, maleic, malonic, tartaric, citric, cyclamic and ascorbic acids.

A preferred species of this invention is that compound or its salts wherein the symbol Y represents the difluoromethyl group.

In addition to the salts indicated above, the term salts is taken to include those internal salts or zwitterions of those compounds of formula I above that are amphoteric in nature. Moreover, whereas the optical configuration for the compounds described herein is not specifically designated, it is recognized that the α-carbon atom possesses an asymmetric center and that individual optical isomers of these compounds exist. Accordingly, both the d- and l-optical isomers as well as the racemic mixtures are contemplated as being within the scope of this invention.

The compounds useful in accordance with the teachings of this invention include the species:

1-fluoromethyl-4-methyl-1,4-butanediamine;
1-difluoromethyl-4-methyl-1,4-butanediamine; and
1-ethynyl-4-methyl-1,4-butanediamine.

Compounds of formula I wherein Y is $CH_2F$ or $CHF_2$ are prepared by reducing a ketone of the formula

wherein Z' is

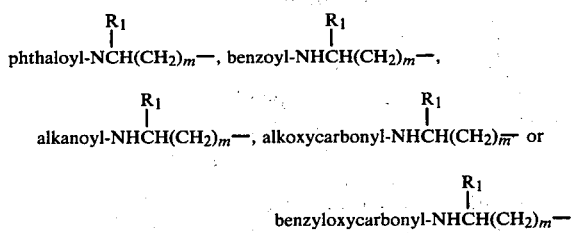

wherein m is an integer 2 or 3, the alkanoyl moiety has from 2 to 5 carbon atoms and is straight or branched, the alkoxy moiety has from 1 to 4 carbon atoms and is straight or branched, Y is $CH_2F$ or $CHF_2$ and $R_1$ is hydrogen or methyl. The ketones are reduced to the corresponding alcohol which is treated with one equivalent of an imide, such as, phthalimide, succinimide or maleimide, 1.1 equivalents of a phosphine, for example, triphenylphosphine or a trialkylphosphine, such as, tri-n-butylphosphine and 1.1 equivalents of diethyl azodicarboxylate in a suitable solvent, such as ethers, for example, diethyl ether, tetrahydrofuran or p-dioxane, benzene or dimethoxyethane at about 0° to 100° C., preferably about 25° C. for about one-half hour to 24 hours under an inert atmosphere, for example, nitrogen or argon and hydrolyzing the thus obtained imido derivative to the free amine.

The compounds of general formula (II) wherein Y is $FCH_2-$ are prepared by treating a compound of the formula

(III)

wherein Z' is defined as above and $R_2$ is a suitable leaving group, such as, halogen, for example, chlorine, bromine or iodine, mesylate, tosylate, triflate or trifluoroacetate with an appropriate fluorinating reagent, such as, potassium fluoride, silver fluoride, cesium fluoride, thallium fluoride, tetrabutylammonium fluoride in a suitable solvent, such as, dimethoxyethane, dimethylsulfoxide, dimethylformamide, ethylene glycol, acetonitrile, acetone, benzene or hydrogen fluoride at a temperature of from about 0° to 200° C. for about 2 to 48 hours. The leaving group $R_2$ may also be a diazo group in which case the fluorinating reagent employed is hydrogen fluoride/pyridine. Suitable solvents for the reaction wherein $R_2$ is a diazo group are aprotic solvents, such as, diethyl ether, tetrahydrofuran and pentane, and the reaction time varies from about 30 minutes to 24 hours at a temperature of about $-20°$ to 65° C. Illustratively, a compound of the formula

as defined above wherein $R_2$ is a diazo group in a suitable aprotic solvent is added to a solution of hydrogen fluoride/pyridine cooled to $-10°$ C. The reaction mixture is stirred vigorously at $-10°$ C. for 1 hour then at about 25° C. for 2 hours then poured on ice. The organic phase is separated, washed with base, for example, sodium bicarbonate, dried over magnesium sulfate and concentrated under vacuum to afford an appropriate fluoromethyl ketone derivative of formula (II).

The diazo ketone derivatives, that is, the compounds of formula (III) wherein $R_2$ is a diazo group, may be obtained from the corresponding acid halide, that is, a compound of the formula

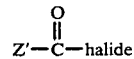

wherein halide may be, for example, chloide and Z' has the meaning defined in formula (II) by slowly adding said acid halide in an aprotic solvent, such as, diethyl ether, tetrahydrofuran, pentane, hexane, benzene, dimethoxyethane or dioxane to a solution of diazomethane cooled to about $-40°$ to 20° C. in ether followed by vigorous stirring at about 25° C. for about 1 to 24 hours. The thus obtained diazo ketone derivative can be isolated by standard procedures, for example, evaporation of the solvent with purification by recrystallization or chromatography or can be treated without isolation with an appropriate fluorinating reagent as described above.

The appropriately substituted diazo ketone derivative described above can also be used to prepare compounds of formula (III) wherein $R_2$ is, for example, halogen, mesylate, tosylate, triflate, or trifluoroacetate by procedures generally known in the art. To obtain compounds of general formula (III) wherein $R_2$ is halogen, such as, chlorine, bromine, or iodine the corresponding compound of formula (III) wherein $R_2$ is a diazo group in a suitable aprotic solvent is treated respectively with aqueous hydrogen chloride, hydrogen bromide or hydrogen iodide. To obtain compounds of formula (III) wherein $R_2$ is mesylate, tosylate, triflate or trifluoroacetate the corresponding diazo ketone derivative, that is, an appropriate compound of formula (III) wherein $R_2$ is a diazo group in a suitable aprotic solvent is treated with dilute sulfuric acid to give the corresponding benzyl methanol ketone derivative which is esterified with an appropriate acid chloride or acid anhydride of methane sulfonic acid, p-toluene sulfonic acid, trifluoromethyl sulfonic acid or trifluoroacetic acid.

The acid halides, that is, compounds of the formula

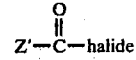

as described above, are known in the art or obtained from the corresponding acids which are known in the art or can be obtained by procedures known in the art by well known procedures, for example, by treatment of the appropriate acid with thionyl chloride in an aprotic solvent, such as, diethyl ether, tetrahydrofuran, benzene or dichloromethane at a temperature ranging from about 0° C. to the reflux temperature of the solvent for about 1 to 24 hours, or treatment of the appropriate acid with oxalyl chloride in an aprotic solvent as illustrated above at a temperature of about 0° to 40° C. for about 1 to 24 hours.

The compounds of general formula (II) wherein Y is $FCH_2-$ and Z' is other than

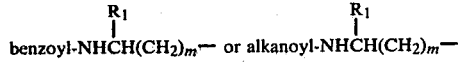

may also be obtained by treating a compound of the formula

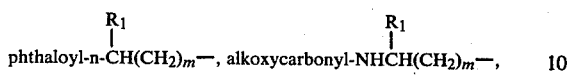

wherein $Z_2$ is phthaloyl-n-$\overset{R_1}{\underset{|}{C}}$H(CH$_2$)$_m$—, alkoxycarbonyl-NH$\overset{R_1}{\underset{|}{C}}$H(CH$_2$)$_m$—, benzyloxycarbonyl-NHCH(CH$_2$)$_m$—, wherein m is the integer 2 or 3 and $R_1$ is hydrogen or lower alkyl of from 1 to 4 carbon atoms with the proviso that when $R_1$ is other than hydrogen m is 2, β-methylthioethyl or β-benzylthioethyl and $R_3$ is halogen, such as, chlorine, bromine or iodine, mesylate or tosylate with triphenylphosphine or tri-(lower)-alkylphosphine, for example, tri-n-butylphosphine, in a solvent such as hydrocarbons, for example, benzene or toluene or lower alcohols, such as, methanol or ethanol or acetonitrile, tetrahydrofuran, diethyl ether or dimethoxyethane at about 25° C. to the reflux temperature of the solvent for about 10 minutes to 48 hours. On cooling a precipitate forms which is washed with solvent and recrystallized using, for example, ethyl acetate, acetonitrile, or a lower alcohol, for example, methanol or ethanol to give the appropriate phosphonium salt. The triphenylphosphonium or trialkylphosphonium salt is added to excess (up to 25%) sodium or lithium metal dissolved in liquid ammonia to which is added a catalytic amount of ferric nitrate with stirring for about 10 minutes to 3 hours after which the ammonia is evaporated under an inert atmosphere, such as, nitrogen or argon. An appropriate solvent, such as, benzene, toluene, diethyl ether, tetrahydrofuran or dimethoxyethane is added and the resulting substituted methylidenephosphorane is collected. The methylidenephosphorane is treated with an ester, such as, a lower alkyl, for example, methyl, ethyl, n-propyl, isopropyl or n-butyl ester of monofluoroacetic acid in a solvent such as benzene, toluene, diethyl ether, tetrahydrofuran or dimethoxyethane under an inert atmosphere such as nitrogen or argon at a temperature of about 0° C. to the reflux temperature of the solvent for about 30 minutes to 24 hours after which the reaction mixture is concentrated and distilled to give the olefin which is treated with aqueous mineral acid, such as hydrochloric or hydrobromic acid or an organic acid such as trifluoroacetic acid or p-toluene sulfonic acid using a cosolvent such as tetrahydrofuran, diethyl ether, or benzene for about 30 minutes to 24 hours at a temperature of from about 0° C. to the reflux temperature of the solvent. The amount of acid employed may vary from a catalytic amount to concentrated acid.

As used in general formula (IV) the term

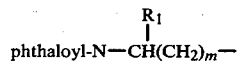

is taken to mean the group

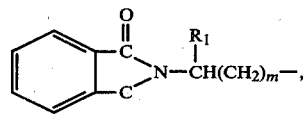

the term

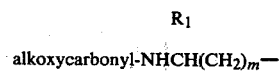

is taken to mean the group

the term

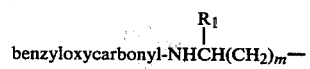

is taken to mean the group

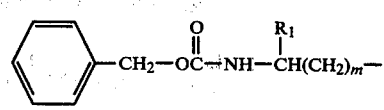

wherein $R_1$ and m have the meanings defined in formula (IV) and alkyl is a straight or branched group of from 1 to 4 carbon atoms.

Compounds of general formula (II) wherein Y is F$_2$CH— are obtained by treating [[(methylsulfinyl)methyl]thio]methane or [[(ethylsulfinyl)methyl]thio]ethane with a suitable strong base followed by alkylation with an appropriate derivative of the formula

wherein Z' has the meaning defined in formula (II) and $R_4$ is halogen, such as, chlorine, bromine or iodine, mesylate or tosylate, treating the thus formed Z' substituted sulfinyl derivative with a suitable strong base followed by alkylation with a suitable halomethylhalo alkylating reagent selected from chlorodifluoromethane, bromodifluoromethane, and difluoriodomethane followed by hydrolysis with aqueous acid.

Suitable strong bases which may be employed in preparing the difluoromethyl substituted ketone derivatives as described above are illustratively, sodium hydride, dilithium acetylide, lithium diisopropylamide, butyllithium, potassium tert-butoxide, sodium tert-butoxide, lithium tert-butoxide, phenyllithium, methyllithium, sodium amide, lithium amide or potassium hydride.

The alkylation reactions described in preparing the difluoromethyl ketone derivatives are carried out in a suitable solvent, such as, tetrahydrofuran, diethyl ether, hexamethylphosphortriamide, dimethylsulfoxide, or benzene at a temperature ranging from about −78° to 65° C. for about 30 minutes to 24 hours. A preferred temperature for the difluoromethyl alkylation step is about 40° C. The alkylated sulfinyl intermediates are isolated by quenching with brine followed by extraction with, for example, diethyl ether, dichloromethane, or benzene.

Hydrolysis of the alkylated sulfinyl derivatives to the ketone is achieved using aqueous mineral acid, such as, hydrochloric, hydrobromic, perchloric or sulfuric in a solvent such as tetrahydrofuran, acetonitrile, diethyl ether or benzene at about −20° to 105° C., preferably about 25° C. for about 30 minutes to 24 hours and preferably about 2 hours. Generally, 0.3 equivalents of mineral acid in 1.5% water is employed. The specific examples contained herein further illustrate the preparation of the difluoromethyl ketone derivatives of formula (II).

The compounds of formulas (IV) and (V) wherein $R_3$ and $R_4$ are hydrogen are known in the art or may be prepared from the appropriate carboxylic acid derivative of the formula $$Z_4-COOH \qquad (VI)$$

wherein $Z_4$ is

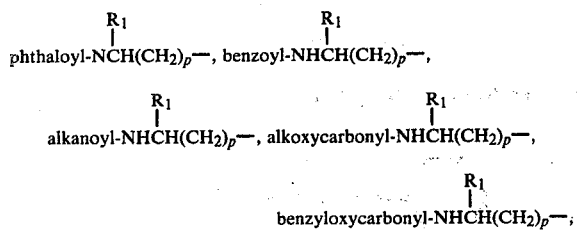

methylthiomethyl or benzylthiomethyl wherein p is the integer 1 or 2, which acids are known in the art or may be obtained by known procedures from the corresponding unprotected amino acids which are known in the art or readily obtained by procedures known in the art. The compounds of formulas (IV) and (V) wherein $R_3$ and $R_4$ are mesylate or tosylate may be prepared by treating the corresponding derivatives wherein $R_3$ and $R_4$ are halogen with a metal salt for example, the sodium salt of methane sulfonic acid or p-toluene sulfonic acid.

Reduction of the ketones of formula (II) to the corresponding alcohol is achieved chemically using, for example, 1 to 10 equivalents of a metal hydride reducing reagent, such as lithium borohydride, sodium borohydride, sodium cyanoborohydride, or lithium aluminum hydride, borane or dimethylthioborane or catalytically using, for example, Raney nickel, rhodium, palladium on charcoal, or platinum oxide. Overall the reaction time varies from about 10 minutes to 24 hours and the temperature varies from about −40° C. to 100° C. depending on the reducing reagent employed. When chemical reduction is employed the reaction time generally varies from about 10 minutes to 24 hours with temperatures varying from about −40° C. to 65° C. Suitable solvents for chemical reduction of compounds of general formula (II) include lower alcohols, such as, methanol or ethanol or ethers, such as, diethyl ether or tetrahydrofuran. When catalytic reduction is employed the reaction time varies from about 1 hour to 24 hours, the reaction temperature varies from about 25° to 100° C. and the pressure varies from 1 to 120 atmospheres.

Hydrolysis to the amine and to remove any distal amine protecting group is achieved using a strong mineral acid, for example, hydrochloric acid, hydrobromic acid or sulfuric acid or an organic acid, for example, toluene sulfonic acid or trifluoroacetic acid in water at reflux temperature for about 4 to 48 hours, or using, for example, 1 to 3 equivalents of hydrazine, methylhydrazine or methylamine at a temperature of from about 25° C. to reflux for about 1 to 12 hours followed by treatment with a strong mineral acid or organic acid as described above.

The compounds of formula (I) wherein Y is C≡CH, or as hereinafter indicated as the alkynyl group, is prepared by treating a suitably protected propargylamine derivative, such as a silyl derivative, with a strong base to form a protected propargylamine carbanion intermediate, which is reacted with an alkylating reagent of the formula $R_5X$ wherein X is halogen, for example, chlorine or bromine, and $R_5$ is $$PhHC=N-CH-(CH_2)_2-,$$
$$\phantom{PhHC=N-}|$$
$$\phantom{PhHC=N-}CH_3$$

and subsequently removing the protecting groups by acid or base hydrolysis as represented by the following reaction scheme:

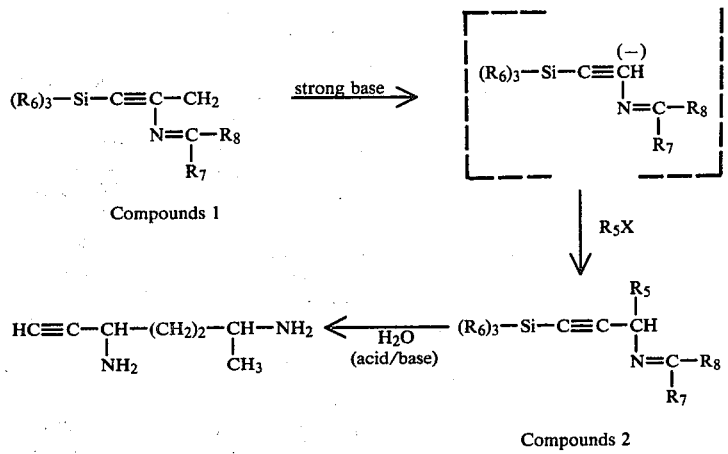

In the above reation scheme $R_5$ and X have the meanings defined hereinabove, Ph represents phenyl; $R_7$ is hydrogen, methoxy or ethoxy, $R_8$ is phenyl, tert-butyl, or triethylmethyl; and $R_6$ is a straight or branched lower alkyl group having from 1 to 4 carbon atoms such as methyl, ethyl, n-propyl and tert-butyl.

Suitable strong bases which may be employed in the above reaction to form each carbanion are those which will abstract a proton from the carbon atom adjacent to the acetylene moiety, such as alkyl lithium, as for example, butyl lithium, phenyl lithium, lithium di-alkylamide, as for example, lithium diisopropylamide, lithium amide, tertiary potassium butylate or sodium amide.

The alkylating reagents, $R_5X$, employed in the above reaction are known in the art or can be prepared by methods known in the art. The reactant

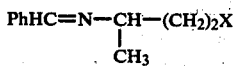

can be prepared, for example, by reacting a 4-chloro or 4-bromoisobutylamine hydrochloride with benzaldehyde in an organic amine, such as triethylamine, in an organic solvent such as diethyl ether, tetrahydrofuran, dioxane, chloroform or dichloromethane.

The alkylating reaction may be carried out in an aprotic solvent, for example, benzene, toluene, ethers, tetrahydrofuran, dimethylsulfoxide, hexamethyl phosphortriamide. The reaction temperature varies from about $-100°$ C. to 25° C., preferably about $-70°$ C., and the reaction time varies from about ½ hour to 24 hours.

Removal of the protecting groups, as represented in the reaction scheme in the step going from compounds 5 to the desired amines, is achieved by treatment with aqueous acid, for example, hydrochloric acid followed by aqueous base, for example, sodium hydroxide or potassium or treatment with phenylhydrazine, hydroxylamine or hydrazine then with aqueous base.

The individual optical isomers of compounds of formula I are resolved use a (+) or (−) binaphthylphosphoric acid salt in accordance with the procedure of R. Viterbo et al., Tetrahedron Letters 48, 4617 (1971). Other resolving agents such as (+) comphor-10-sulfonic acid may also be employed.

The compounds described herein are useful for their ability to inhibit the growth of algae. At present, copper sulfate is a commonly employed algicide. In alkaline water copper sulfate quickly precipitates as copper carbonate and more slowly as copper hydrate. Moreover, certain algae, as for example, the green alga Scenedesmus and the blue-green alga Chlorella are resistant to copper sulfate toxicity. Inasmuch as copper sulfate operates via a toxic resonse to algae, there still remain the difficult problems of odor, water palatability and the removal of dead and decomposing algae.

Thus, there is a need for economically feasible chemical compounds that are non-toxic to plants and animal life. It would further be highly desirable to have a biological agent which would effectively inhibit the growth and proliferation of algae in recreational and industrial water supplies, therby eliminating, at the same time, the ancillary problems associated with dead and dying algae.

The α-substitured amines of general formula (I) above are useful in controlling the growth of algae, e.g., in ponds, lakes, reservoirs, raw water supplies, water-treating plants, water-cooling towers, recreational waters, fish ponds and aquariums. Moreover, these compounds are effective in inhibiting algal growth of the major groups of algae, i.e., the blue-green algae, green algae, diatom algae and flagellate algae.

It is not exactly known how the compounds of this invention are able to inhibit the growth of algae. Inter alia, these compounds are irreversible inhibitors of ornithine decarboxylase. As irreversible inhibitors of this decarboxylase enzyme, these compounds inhibit polyamine formation which may be required for algal cell division. In any event, the practice of this invention is not limited to any particular mode or theory of action whereby the compounds of this invention are able to effectively inhibit the growth of algae.

The effect of the compounds of general formula (I) above upon algal growth can be demonstrated by incubating the algae to be tested in a standard culture medium and room temperature and comparing the cell growth of the treated algae with the corresponding untreated control cultures. Cell growth and/or inhibition is determined by a comparison of the total cell weight, as illustrated in Example 5 below.

When dealing with large volumes of water such as lakes, reservoirs, or industrial water supplies, the α-substituted amines of general formula (I) above can be utilized by casting the compounds directly upon the surface of such waters. Preferably, when utilized in this fashion, the compunds are formulated in a granular form. Alternatively, when dealing with smaller volumes of water, the compounds described herein can be dissolved in water to form a concentrate or stock solution, thereby permitting a more accurate control of the amount of compound to be administered.

The compounds described herein can be favorably employed at concentrations ranging from about 0.01 mg/ml to about 25 mg/ml. Preferably, a concentration of from 2 mg/ml to 15 mg/ml of active ingredient is employed.

The invention described herein is more particularly illustrated in conjunction with the following examples specifically describing how the compounds of this invention may be prepared and used.

EXAMPLE 1

1-Fluoromethyl-4-methyl-1,4-butanediamine dihydrochloride

To a solution of 40 mmole of diazomethane in 110 ml of ether cooled to 0° C. and magnetically stirred is added under nitrogen dropwise over a period of 1 hour a solution of 20 ml of 4-phthalimido-4-methylbutyryl chloride in 75 ml of ether. Stirring is continued for 1 hour at 25° C. after which the reaction mixture is added to a solution of 40 ml of HF/pyridine precooled to 0° C. The resulting heterogeneous mixture is stirred at 25° C. for 1½ hours and then poured on ice water. The ether phase is separated, washed with a solution of bicarbonate, then with brine and dried over magnesium sulfate. Concentration of the solvent under reduced pressure affords a solid which is recrystallized from diethylether/pentane to give fluoromethyl 3-phthalimido-3-methylpropyl ketone.

To a solution of 550 mg (2.2 mmole) of fluoromethyl 3-phthalimido-3-methylpropyl ketone in a mixture of 5 ml of tetrahydrofuran and 5 ml of methanol cooled to $-20°$ C. is added a solution of 0.8 mmole of sodium borohydride in a mixture of 5 ml of tetrahydrofuran and 5 ml of methanol precooled to $-20°$ C. The reaction mixture is stirred for 15 minutes at $-20°$ C. and then neutralized with 2 M HCl to a pH of 1. The solvents are evaporated under reduced pressure and the residue is partitioned between water and chloroform. The organic phase is washed and brine, dried over magnesium sulfate and concentrated to give a residue which is recrystallized from tetrahydrofuran-diethylether to afford 1-fluoro-5-phthalimido-5-methyl-2-pentanol. A mixture of 264 mg (1.05 mmole) of 1-fluoro-5-phthalimido-5-methylpentanol, 170 mg (1.05 mmole) of the phthalimide, 302 mg (1.05 mmole) of triphenylphosphine and 201 mg (1.15 mmole) of diethylazodicarboxylate in 8 ml of tetrahydrofuran is stirred under nitrogen for 2 hours at 25° C. The solvent is evaporated under reduced pressure and the residue taken up in benzene. The insoluble material is discarded and the residue obtained after concentration of the filtrate is recrystallized from tetrahydrofurandiethylether to give 1-fluoromethyl-4-methyl-1,4-butanediyl-bis-phthalimide. A suspension of 3.1 g of 1-fluoromethyl-4-methyl-1,4-butanediyl-bis-phthalimide in 140 ml of concentrated HCl is heated at reflux temperature for 3 days. The phthalic acid which precipitates on cooling to 4° C. is filtered off. The filtrate is concentrated to about 20 ml and cooled to 4° C. The remaining phthalic acid which separates is filtered off and the filtrate is concentrated under reduced pressure. The residue is treated with 40 ml of boiling isopropyl alcohol 3 times and then recrystallized from absolute ethanol to give 1-fluoromethyl-4-methyl-1,4-butanediamine dihydrochloride.

EXAMPLE 2

1-Ethynyl-4-methyl-1,4-butanediamine

To 10.8 g (0.05 M) of 3-trimethylsilylprop-2-ynyl-1-iminobenzyl in 500 ml of tetrahydrofuran under nitrogen atmosphere at −78° C. is added n-butyllithium (0.05 M). After 10 minutes the dark red carbanion is treated with 11.3 g (0.05 M) of 3-iodo-3-methylpropyl-1-iminobenzyl in 20 ml of tetrahydrofuran. After 3 hours at −78° C., 50 ml of water is added and the tetrahydrofuran is evaporated leaving a residue which is heated at reflux under nitrogen atmosphere with 100 ml of 6 N hydrochloric acid for 48 hours. Upon cooling the aqueous solution is washed with methylene chloride, made alkaline with aqueous sodium hydroxide and reextracted with methylene chloride. The methylene chloride extract is dried over magnesium sulfate, filtered, concentrated and distilled to afford 1-ethynyl-4-methyl-1,4-butanediamine, b.p. 50° C./0.4 mm.

EXAMPLE 3

Granules suitable for distribution over large areas of water are prepared as follows.

|  | Grams |
| --- | --- |
| 1-difluoromethyl-4-methyl-1,4-butanediamine | 33.0 |
| Corn starch | 18.5 |
| Lactose | 48.2 |
| Zinc stearate | 0.3 |
|  | 100.0 |

The 1-difluoromethyl-4-methyl-1,4-butanediamine and approximately 6 to 9 grams of the lactose are mixed and passed through a fluid energy mill or micronizer to give a particle powder size of approximately 1–25 microns. Water, 35 ml, is added to approximately 2.0 grams of the corn starch and blended to prepare a 5% starch paste. The micronized pentanoic acid-lactose powder, the remaining lactose and the remaining corn starch are well blended, the starch paste added and blended, and the resulting mixture passed through a No. 12 mesh screen. The resulting granules are dried at 38° C. to a moisture content of approximately 3%. The dried granules are ground through a U.S. Standard No. 12 screen and lubricated by mixing with 0.3 grams of zinc stearate.

EXAMPLE 4

A 20% stock solution of algae inhibitor for use in aquariums is prepared by dissolving 75.7 grams of 1-fluoromethyl-4-1,4-butanediamine in one gallon of water. The addition of 90 ml of this stock solution to each gallon of water is sufficient to provide an effective algae inhibiting concentration of 4.8 mg/ml.

EXAMPLE 5

Ten ml of a culture of blue-green algae, *Phormidium inundatum* culture 1098, obtained from the Environmental Monitoring and Support Laboratory, U.S. Environmental Protection Agency, Cincinnati, Ohio, is diluted with 320 ml of freshly prepared modified Chu. No. 10 culture media that had been 0.22 μm filter-sterilized, and which contained the following:

| Chemical | gms/liter |
| --- | --- |
| $Ca(NO_3)_2 \cdot 4H_2O$ | 0.232 |
| $K_2HPO_4$ | 0.01 |
| $MgSO_4 \cdot 7H_2O$ | 0.025 |
| $Na_2CO_3$ | 0.02 |
| $Na_2SiO_3 \cdot 5H_2O$ | 0.044 |
| Ferric citrate | 0.0035 |
| Citric acid | 0.0035 | and included the following trace elements:

| | |
| --- | --- |
| $H_3BO_3$ | $2.4 \times 10^{-3}$ |
| $MnCl_2 \cdot 4H_2O$ | $1.4 \times 10^{-3}$ |
| $ZnCl_2$ | $4.0 \times 10^{-4}$ |
| $CoCl_2 \cdot 6H_2O$ | $2.0 \times 10^{-5}$ |
| $CuCl_2 \cdot 2H_2O$ | $1.0 \times 10^{-7}$ |

The culture is uniformly mixed and 50 ml of this suspension is added to each of six 125 ml spinner flasks containing 1-ethynyl-4-methyl-1,4-butanediamine or water to give final concentrations of 10 mM, 5 mM or 0 mM (control).

Each concentration is run in duplicate and incubated under direct fluorescent light at room temperature. The cultures and test compound are continuously exposed to a 150–170 foot candle fluorescent source of light of constant intensity and observed over a period of 10 days. After 10 days the culture is harvested via centrifugation, the supernatant solution removed, and the algal residue dried overnight in a vacuum oven.

At the time of harvest there was visibly more growth on the control sample than in the 5 mM samples, and visibly more growth in the 5 mM samples than in the 10 mM samples. The weights observed are expressed in grams.

| Concentration of 1-ethylenyl-4-methyl-1,4-butanediamine | Grams |
| --- | --- |
| 0 mM (control) | 0.271 |
| 5 mM | 0.0116 |
| 10 mM | 0.0056 |

I claim:
1. A method of inhibiting the growth of algae which comprises contacting said algae with an algal inhibiting amount of an α-substituted amine having the formula

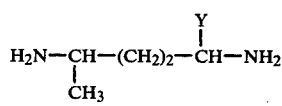

wherein

Y is selected from the group consisting of $CH_2F$, $CHF_2$ and $C\equiv CH$; and the salts and individual optical isomers thereof.

2. A method according to claim 1 wherein Y is $CHF_2$.

3. A method according to claim 1 wherein Y is $CH_2F$.

4. A method according to claim 1 wherein Y is $C\equiv CH$.

5. A method according to claim 1 wherein the α-substituted amine is in solution at a concentration of from 0.01 mg/ml to 25 mg/ml.

* * * * *

UNITED STATES PATENT AND TRADEMARK OFFICE
CERTIFICATE OF CORRECTION

PATENT NO. : 4,437,873

DATED : March 20, 1984

INVENTOR(S) : Albert Sjoerdsma

It is certified that error appears in the above-identified patent and that said Letters Patent is hereby corrected as shown below:

At Column 2, line 6, the patent reads "compunds" and should read --compounds--.

At Column 6, line 5, the patent reads

"alkoxycarbonyl-NHCH(CH2)m-" and should read: "alkoxycarbonyl-NHCH(CH2)m-" with $R_1$ substituent At Column 8, line 56, the patent reads "reation" and should read --reaction--.

At Column 9, line 29, the patent reads "are resolved use a (+)" and should read --are resolved using a (+)--.

At Column 9, line 32, the patent reads "comphor-" and should read --camphor- --.

At Column 9, line 42, the patent reads "resonse" and should read --response--.

At Column 9, line 50, the patent reads "therby" and should read --thereby--.

At Column 10, line 61, the patent reads "phase is washed and brine, dried" and should read --phase is washed in brine, dried--.

At Column 12, line 5, Example 4, the patent reads "fluoromethyl-4-1,4-" and should read --fluozomethyl-- ⊢methyl-1,4- --.

UNITED STATES PATENT AND TRADEMARK OFFICE
CERTIFICATE OF CORRECTION

PATENT NO. : 4,437,873
DATED : March 20, 1984
INVENTOR(S) : Albert Sjoerdsma

It is certified that error appears in the above-identified patent and that said Letters Patent are hereby corrected as shown below:

At Column 12, line 59, third table, the patent reads "Concentration of 1-ethylenyl-" and should read -- Concentration of 1-ethynyl- --.

Signed and Sealed this

Twenty-fourth Day of January, 1995

BRUCE LEHMAN

*Attest:*

*Attesting Officer*   Commissioner of Patents and Trademarks